(12) United States Patent
Park et al.

(10) Patent No.: US 10,293,335 B2
(45) Date of Patent: May 21, 2019

(54) RH-C₃N₄ HETEROGENEOUS CATALYST FOR PREPARING ACETIC ACID BY CARBONYLATION REACTION

(71) Applicants: KOREA RESEARCH INSTITUTE OF CHEMICAL TECHNOLOGY, Daejeon (KR); RESEARCH BUSINESS FOUNDATION SUNGKYUNKWAN UNIVERSITY, Suwon-si, Gyeonggi-do (KR)

(72) Inventors: Jae Hyun Park, Anyang-si (KR); Jong Wook Bae, Suwon-si (KR); Tae Sun Chang, Daejeon (KR); Beom Sik Kim, Daejeon (KR)

(73) Assignees: KOREA RESEARCH INSTITUTE OF CHEMICAL TECHNOLOGY, Daejeon (KR); RESEARCH BUSINESS FOUNDATION SUNGKYUNKWAN UNIVERSITY, Suwon-si (KR)

(*) Notice: Subject to any disclaimer, the term of this patent is extended or adjusted under 35 U.S.C. 154(b) by 0 days.

(21) Appl. No.: 15/540,497

(22) PCT Filed: Aug. 24, 2015

(86) PCT No.: PCT/KR2015/008824
§ 371 (c)(1),
(2) Date: Jun. 28, 2017

(87) PCT Pub. No.: WO2016/108389
PCT Pub. Date: Jul. 7, 2016

(65) Prior Publication Data
US 2018/0001311 A1 Jan. 4, 2018

(30) Foreign Application Priority Data
Dec. 29, 2014 (KR) .................. 10-2014-0192058

(51) Int. Cl.
| | |
|---|---|
| *C07C 51/12* | (2006.01) |
| *C07C 53/08* | (2006.01) |
| *B01J 31/18* | (2006.01) |
| *B01J 31/28* | (2006.01) |
| *B01J 27/24* | (2006.01) |
| *B01J 35/00* | (2006.01) |
| *B01J 35/10* | (2006.01) |
| *B01J 37/02* | (2006.01) |
| *B01J 21/18* | (2006.01) |
| *B01J 23/46* | (2006.01) |
| *B01J 37/08* | (2006.01) |

(52) U.S. Cl.
CPC ............ *B01J 31/181* (2013.01); *B01J 21/18* (2013.01); *B01J 23/464* (2013.01); *B01J 27/24* (2013.01); *B01J 31/18* (2013.01); *B01J 31/28* (2013.01); *B01J 35/0006* (2013.01); *B01J 35/1009* (2013.01); *B01J 35/1014* (2013.01); *B01J 35/1019* (2013.01); *B01J 37/0221* (2013.01); *B01J 37/0236* (2013.01); *C07C 51/12* (2013.01); *B01J 37/084* (2013.01); *B01J 2231/321* (2013.01); *B01J 2531/822* (2013.01)

(58) Field of Classification Search
USPC ........................................... 562/519
See application file for complete search history.

(56) References Cited

U.S. PATENT DOCUMENTS

| | | | |
|---|---|---|---|
| 3,769,329 | A | 10/1973 | Paulik et al. |
| 5,334,755 | A | 8/1994 | Yoneda et al. |
| 5,364,963 | A | 11/1994 | Minami et al. |
| 5,576,458 | A | 11/1996 | Minami et al. |

FOREIGN PATENT DOCUMENTS

| | | |
|---|---|---|
| EP | 0643034 A1 | 3/1995 |
| EP | 0728726 A1 | 8/1996 |
| EP | 0752406 A1 | 1/1997 |
| EP | 2559680 A1 | 2/2013 |
| KR | 10-1992-0020188 | 4/1996 |
| KR | 10-0176417 | 3/1999 |
| KR | 10-0278950 | 1/2001 |
| KR | 10-2006-0122944 | 5/2012 |

OTHER PUBLICATIONS

Zhang, Jan. 1, 2014 "Synthesis and modification of semiconductor/co-catalyst systems for photo(electro)chemical reactions" p. 83.*
Zhang et al International Journal of Hydrogen Energy, year 2014, 39, pp. 11537-11546.*
Borah, B.J. et al., "Dicarbonylrhodium(I) Complexes of Benzoylpyridine Ligands: Synthesis, Reactivity and Catalytic Carbonylation Reaction", Journal of Molecular Catalysis A: Chemical, vol. 319, p. 66-70 (2010).
"Synthesis of acetic acid by carbonylation of methanol on heterogenized homogeneous catalysts", Chemical Engineering and Materials Research Information Center, One page.
Kim, J.H., et al., "Hollow Spherical Carbon with Mesoporous Shell as a Superb Anode Catalyst Support in Proton Exchange Membrane fuel Cell", Catalysis Today, vol. 146, p. 25-30 (2009).
International Preliminary Report on Patentability for International Patent Application No. PCT/KR2015/008824 dated Jul. 4, 2017, 13 pages.

* cited by examiner

*Primary Examiner* — Ana Z Muresan
(74) *Attorney, Agent, or Firm* — Morgan, Lewis & Bockius LLP

(57) ABSTRACT

This invention relates to a heterogeneous catalyst represented by Rh/C₃N₄ configured such that a complex of a rhodium compound and 3-benzoylpyridine is immobilized on a carbon nitride support.

4 Claims, 1 Drawing Sheet

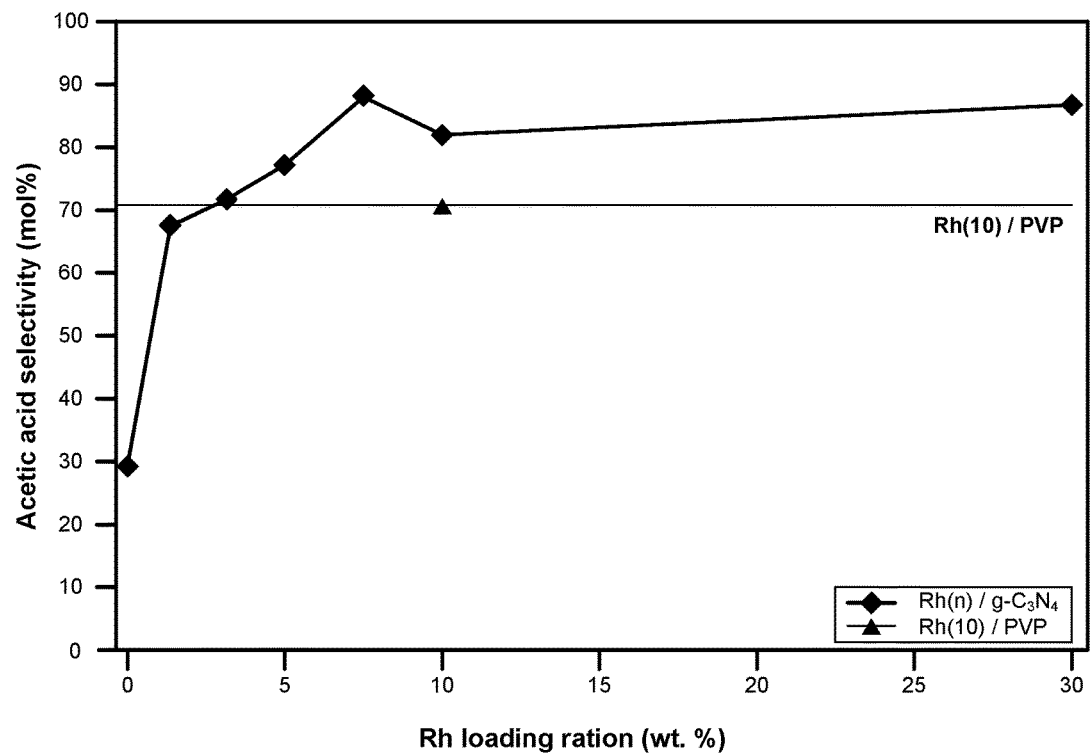

RH-C₃N₄ HETEROGENEOUS CATALYST FOR PREPARING ACETIC ACID BY CARBONYLATION REACTION

CROSS-REFERENCE TO RELATED APPLICATIONS

This application is a U.S. National Phase of International Patent Application No. PCT/KR2015/008824, filed on Aug. 24, 2015, which claims priority to Korean Application No. 10-2014-0192058, filed on Dec. 29, 2014, the disclosures of which are incorporated herein by reference in their entirety for all purposes.

TECHNICAL FIELD

The present invention relates to a catalyst for use in the preparation of acetic acid through a methanol carbonylation reaction using carbon monoxide, and particularly to a heterogeneous catalyst represented by $Rh/C_3N_4$, configured such that a complex of a rhodium compound and 3-benzoylpyridine is immobilized on a carbon nitride support.

BACKGROUND ART

Acetic acid, which is a fundamental chemical, is an important chemical widely useful in the petrochemical, polymer chemistry, organic chemistry, medicine, and pesticide fields. Among variously known methods of preparing acetic acid, particularly useful is the preparation of acetic acid through a methanol carbonylation reaction using carbon monoxide.

Conventional methods of preparing acetic acid through a methanol carbonylation reaction include 1) a Monsanto process mainly using rhodium (Rh), commercialized in the 1960s [Patent Document 1]; 2) a Cativa process mainly using iridium (Ir), commercialized in the 1990s [Patent Documents 2 to 4]; and 3) an Acetica process using a heterogeneous catalyst configured such that a rhodium (Rh) catalyst is immobilized on a polymer [Patent Documents 5 to 7]. Although the above processes are satisfactory in reactant conversion and selectivity, they suffer from the aspect of use of energy, i.e. the consumption of a large amount of energy for the separation process for catalyst recycling and for the byproduct treatment process. In particular, the Monsanto and Cativa processes using the homogeneous catalyst in which catalyst recycling is limited are regarded as unprofitable at present, and the Acetica process using the heterogeneous catalyst is receiving a great deal of attention, and thus the number of research reports related thereto is gradually increasing.

Taking into consideration the fact that a methanol carbonylation reaction is carried out in a liquid state, the Acetica process is advantageous because the loss of the catalyst may be minimized due to the physical adsorption of the rhodium precious metal onto the polymer support. However, with regard to the heterogeneous catalytic reaction using the polymer support, there has been reported that the activity of the catalyst is slightly decreased compared to the homogenous catalytic reaction. Recently, the use of a support having a structure of activated carbon or hydrotalcite in lieu of the polymer support has been proposed. [Patent Document 8]

Also, thorough research is ongoing into minimizing the loss of rhodium precious metal and controlling the interaction between the rhodium active component and the support to thus increase the stability and dispersibility of the catalyst.

In this regard, Non-Patent Document 1 discloses a technique for immobilizing, on the support, a rhodium complex using 3-benzoylpyridine as a functional group for optimizing the rhodium-support interaction.

CITATION LIST

Patent Literature (Patent Document 1) U.S. Pat. No. 3,769,329
(Patent Document 2) European Patent Application Publication No. 643,034
(Patent Document 3) European Patent Application Publication No. 728,726
(Patent Document 4) European Patent Application Publication No. 752,406
(Patent Document 5) U.S. Pat. No. 5,334,755
(Patent Document 6) U.S. Pat. No. 5,364,963
(Patent Document 7) U.S. Pat. No. 5,576,458
(Patent Document 8) European Patent Application Publication No. 2,559,680

Non-Patent Literature (Non-Patent Document 1) Journal of molecular catalysis A: chemical 319 (2010) 66

DISCLOSURE

Technical Problem

A first aspect of the present invention is to provide a novel catalyst, in which mesoporous carbon nitride having a fine pore structure is used as a support and a rhodium (Rh) active metal is complexed with a 3-benzoylpyridine ligand and immobilized, thereby increasing methanol conversion and an acetic acid yield when applied to a methanol carbonylation reaction.

A second aspect of the present invention is to provide a method of preparing the novel catalyst.

A third aspect of the present invention is to provide a method of preparing acetic acid through a methanol carbonylation reaction using carbon monoxide in the presence of the novel catalyst.

Technical Solution

In order to accomplish the above aspects, the present invention provides a heterogeneous catalyst represented by $Rh/C_3N_4$, which is used for the preparation of acetic acid through a methanol carbonylation reaction using carbon monoxide and is configured such that a rhodium complex, serving as an active material and comprising a rhodium compound and 3-benzoylpyridine complexed with each other, is immobilized on a carbon nitride support.

In addition, the present invention provides a method of preparing a heterogeneous catalyst, comprising: (S1) preparing a carbon nitride support by heating a melamine resin serving as a carbon source to 500 to 550° C. in a nitrogen atmosphere; (S2) preparing a rhodium complex by reacting a rhodium compound with 3-benzoylpyridine; and (S3) preparing a heterogeneous catalyst represented by $Rh/C_3N_4$ by immobilizing, on the carbon nitride support prepared in (Si), the rhodium complex prepared in (S2).

In addition, the present invention provides a method of preparing acetic acid, comprising subjecting methanol to a carbonylation reaction using carbon monoxide in the presence of the heterogeneous catalyst represented by $Rh/C_3N_4$.

Advantageous Effects

According to the present invention, an $Rh/C_3N_4$ heterogeneous catalyst is configured such that a complex of a rhodium active metal and a 3-benzoylpyridine ligand is immobilized on carbon nitride, thereby exhibiting high catalytic activity while minimizing the use of active metal due to the strong catalytic activity of the rhodium complex alone and the strong interaction between rhodium and the carbon nitride support.

Also, according to the present invention, the $Rh/C_3N_4$ heterogeneous catalyst facilitates separation of the catalyst from a liquid reaction system, and is thus more favorable from the aspect of commercialization of the catalyst process.

Therefore, the $Rh/C_3N_4$ heterogeneous catalyst of the invention is particularly useful in the mass production of acetic acid through a methanol carbonylation reaction using carbon monoxide.

BRIEF DESCRIPTION OF DRAWING

FIG. 1 is a graph showing the reaction activity (acetic acid selectivity) depending on the amount of a rhodium complex upon the methanol carbonylation reaction using an $Rh/C_3N_4$ heterogeneous catalyst of the present invention.

BEST MODE

The present invention addresses an $Rh/C_3N_4$ heterogeneous catalyst useful for the preparation of acetic acid through a methanol carbonylation reaction using carbon monoxide.

The $Rh/C_3N_4$ catalyst of the present invention is a heterogeneous catalyst configured such that a complex of a rhodium compound and 3-benzoylpyridine is immobilized on a carbon nitride support.

In the present invention, carbon nitride ($C_3N_4$) is used as the support. Carbon nitride has a chemical formula of $C_3N_4$, and alpha-, beta-, cubic, pseudocubic, and graphitic carbon nitrides are reported, and have different three-dimensional structures, but may be collectively referred to as carbon nitride. Also, carbon nitride is synthesized in the form of a film, a hollow sphere, or a nanotube, and recently graphitic carbon nitride has been synthesized, which is nitrogen-rich and in which spherical pores having a macro size are regularly arranged and are interconnected in a three-dimensional manner by means of connective pores having a meso size.

In the present invention, the selection of carbon nitride serving as the support is not particularly limited. In order to improve the dispersibility of the rhodium complex and ensure the carbonylation reactivity of the support alone, a carbon nitride support having a specific surface area of 5 to 250 $m^2/g$ is preferably used.

Carbon nitride plays a leading role in causing the catalyst-reactant interaction from electron transfer due to the large amount of internal Lewis acid sites thereof, and may thus function as a quasi metal. Also, carbon nitride having a large number of Lewis acid sites may have a positive effect on adsorption to a metal as well as the function as the catalyst. Specifically, an active material, that is, a metal element or a rhodium complex, may be more easily immobilized on the carbon nitride support, and uniform dispersion of the active material on the carbon nitride support is possible. Furthermore, carbon nitride having a large number of Lewis acid sites may interact with the rhodium complex serving as the active material to thus suppress the aggregation or leaching of the rhodium complex. Accordingly, the catalyst of the present invention, configured such that the rhodium complex is immobilized as the active material on the carbon nitride support, is able to suppress the deactivation of the rhodium complex to thereby ensure stable long-term performance of the catalyst.

Useful as the active material in the present invention is a rhodium complex configured such that the rhodium compound is complexed with 3-benzoylpyridine.

Specifically, the rhodium complex may be immobilized in an amount of 5 to 30 wt % based on the weight of the carbon nitride support. Here, if the amount of the rhodium complex is less than 5 wt %, desired catalytic activity cannot be obtained. On the other hand, if the amount thereof exceeds 30 wt %, the catalyst preparation costs may increase due to the use of expensive rhodium (Rh), thus negating economic benefits, which is undesirable. Hence, the catalyst has to be prepared so that the rhodium complex is contained in an amount falling in the range of the present invention.

In addition, the present invention addresses a method of preparing the $Rh/C_3N_4$ heterogeneous catalyst.

The method of preparing the catalyst according to the present invention includes (S1) preparing a carbon nitride support by heating a melamine resin serving as a carbon source to 500 to 550° C. in a nitrogen atmosphere; (S2) preparing a rhodium complex by reacting a rhodium compound with 3-benzoylpyridine; and (S3) preparing a heterogeneous catalyst represented by $Rh/C_3N_4$ by immobilizing, on the carbon nitride support prepared in (S1), the rhodium complex prepared in (S2).

The method of preparing the catalyst according to the present invention is described in detail below.

(S1) is a step of preparing the carbon nitride support by heating a melamine resin, serving as a carbon source, to 500 to 550° C. in a nitrogen atmosphere.

In the preparation of the carbon nitride support, a carburization process is applied, and gradual heating is performed with a temperature gradient. Specifically, the carbon nitride support is prepared by heating the melamine resin in powder form, serving as the carbon source, in a nitrogen atmosphere in a manner in which the reaction temperature is increased to 200 to 250° C. at a heating rate of 1 to 3° C./min, maintained for 20 to 40 min, further increased to 300 to 350° C. at a heating rate of 1 to 3° C./min, maintained for 20 to 40 min, additionally increased to 500 to 550° C. at a heating rate of 1 to 3° C./min, and maintained for 200 to 300 min.

The melamine resin is subjected to condensation and thermal decomposition under conditions of the heating rate and the heating temperature gradient during the preparation of the support to give a carbon nitride support in powder form through rearrangement of carbon and nitrogen.

(S2) is a step of preparing the rhodium complex, serving as an active material.

The rhodium complex is prepared through complexation of a rhodium compound and 3-benzoylpyridine. Specifically, dichloro tetracarbonyl dirhodium ($O_4C_4Cl_2Rh_2$) is dissolved in a dichloromethane ($CH_2Cl_2$) solvent, a 3-benzoylpyridine ($C_6H_5COC_5H_4N$) ligand is dissolved therein, and a wet impregnation process is performed to give a rhodium complex. Here, 3-benzoylpyridine, serving as the ligand, is used at a molar ratio of 0.5 to 2.0 relative to the rhodium metal. After the completion of the reaction, an aging process is conducted for about 1 hr, drying is performed under reduced pressure to remove the solvent, and then the prepared rhodium complex is washed with hexane (n-hexane, $C_6H_{14}$). The rhodium complex thus washed is dried at room temperature for about 12 to 24 hr.

(S3) is a step of preparing the heterogeneous catalyst by immobilizing the rhodium complex acting as the active material on the carbon nitride support.

Specifically, the carbon nitride support and the rhodium complex are added to a dichloromethane solvent, stirred for 2 to 5 hr using an impregnation process at room temperature, dried under reduced pressure to remove the dichloromethane solvent, and dried at room temperature for about 12 to 24 hr, thus yielding an $Rh/C_3N_4$ heterogeneous catalyst in powder form.

In addition, the present invention addresses a method of preparing acetic acid, comprising subjecting methanol to a carbonylation reaction using the heterogeneous catalyst represented by $Rh/C_3N_4$.

The carbonylation reaction is carried out in a manner in which methanol and carbon monoxide are used as reaction materials, and the activity promoter iodomethane ($CH_3I$) and deionized water are used. Specifically, the molar ratio of methanol/iodomethane/deionized water serving as liquid reactants falls in the range of (10 to 80)/(10 to 60)/(10 to 30). As the reactants, methanol and carbon monoxide are used at a molar ratio of $[CO]/[CH_3OH]>0.6$, and preferably the molar ratio of $[CO]/[CH_3OH]$ falls in the range of 0.5 to 10.0 in order to increase the reaction rate and the acetic acid selectivity. Also, the molar ratio of carbon monoxide and nitrogen gas as the internal standard material falls in the range of $CO:N_2=90:10$. The carbonylation reaction is carried out at a reaction temperature of 50 to 200° C. under a reaction pressure of 10 to 70 bar in order to increase the reaction rate and acetic acid selectivity.

A better understanding of the present invention is given through the following Examples, which are set forth to illustrate but are not to be construed as limiting the scope of the present invention.

EXAMPLE

Example 1

Preparation of $Rh(5)/C_3N_4$ Heterogeneous Catalyst

1) Preparation of Carbon Nitride Support 10 g of a melamine powder was placed in a tube reactor, and a heating reaction was carried out while nitrogen gas was allowed to flow at a flow rate of 50 mL/min. For the heating reaction, the reaction temperature was increased to 250° C. from room temperature at a heating rate of 1.9° C./min, maintained at 250° C. for 30 min, further increased to 350° C. from 250° C. at a heating rate of 1.7° C./min, maintained at 350° C. for 30 min, additionally increased to 550° C. from 350° C. at a heating rate of 3.3° C./min, and maintained at 550° C. for 240 min. The carburization process was slowly performed in this way, thus obtaining a carbon nitride support in powder form having a specific surface area of 12.8 eg.

2) Preparation of Rhodium Complex 0.652 g of dichloro tetracarbonyl dirhodium ($O_4C_4Cl_2Rh_2$) was dissolved in 30 mL of dichloromethane, and 0.6271 g of a 3-benzoylpyridine ($C_6H_5C0O_5H_4N$) ligand was dissolved therein. The resulting solution was aged at room temperature (about 25° C.) for about 1 hr, dried under reduced pressure to remove the solvent, and then washed with 30 mL of hexane. After the completion of the hexane washing process, drying was performed at room temperature for 24 hr or more, thus obtaining a rhodium complex.

3) Preparation of Heterogeneous Catalyst 0.020 g of the rhodium complex and 0.380 g of the carbon nitride support, prepared as described above, were dissolved in 30 mL of dichloromethane and then stirred at room temperature at a stirring rate of 180 rpm for 2 hr. Drying under reduced pressure to remove the dichloromethane solvent and further drying at room temperature for 12 hr or more were conducted, thus obtaining a catalyst in powder form.

The finally prepared catalyst is a heterogeneous catalyst configured such that the rhodium complex is immobilized on the carbon nitride support, the amount of the rhodium complex being 5 wt % based on the weight of the support. The catalyst prepared by the method of Example 1 was represented by $Rh(5)/C_3N_4$.

Example 2

Preparation of $Rh(7)/C_3N_4$ Heterogeneous Catalyst

A heterogeneous catalyst was prepared in the same manner as in Example 1, with the exception that 0.028 g of the rhodium complex and 0.372 g of the carbon nitride support were used in 3) of Example 1 so that the amount of the rhodium complex was 7 wt % based on the weight of the support. The catalyst prepared by the method of Example 2 was represented by $Rh(7)/C_3N_4$.

Example 3

Preparation of $Rh(10)/C_3N_4$ Heterogeneous Catalyst

A heterogeneous catalyst was prepared in the same manner as in Example 1, with the exception that 0.040 g of the rhodium complex and 0.360 g of the carbon nitride support were used in 3) of Example 1 so that the amount of the rhodium complex was 10 wt % based on the weight of the support. The catalyst prepared by the method of Example 3 was represented by $Rh(10)/C_3N_4$.

Example 4

Preparation of $Rh(30)/C_3N_4$ Heterogeneous Catalyst

A heterogeneous catalyst was prepared in the same manner as in Example 1, with the exception that 0.120 g of the rhodium complex and 0.280 g of the carbon nitride support were used in 3) of Example 1 so that the amount of the rhodium complex was 30 wt % based on the weight of the support. The catalyst prepared by the method of Example 4 was represented by $Rh(30)/C_3N_4$.

Comparative Example 1

Preparation of $Rh(0)/C_3N_4$ Heterogeneous Catalyst

The carbon nitride prepared in 1) of Example 1 was directly used as a catalyst, and the corresponding catalyst was represented by $Rh(0)/C_3N_4$.

Comparative Example 2

Preparation of $Rh(1)/C_3N_4$ Heterogeneous Catalyst

A heterogeneous catalyst was prepared in the same manner as in Example 1, with the exception that 0.004 g of the rhodium complex and 0.396 g of the carbon nitride support were used in 3) of Example 1 so that the amount of the rhodium complex was 1 wt % based on the weight of the support. The catalyst prepared by the method of Comparative Example 2 was represented by Rh(1)/C$_3$N$_4$.

Comparative Example 3

Preparation of Rh(3)/C$_3$N$_4$ Heterogeneous Catalyst

A heterogeneous catalyst was prepared in the same manner as in Example 1, with the exception that 0.012 g of the rhodium complex and 0.388 g of the carbon nitride support were used in 3) of Example 1 so that the amount of the rhodium complex was 3 wt % based on the weight of the support. The catalyst prepared by the method of Comparative Example 3 was represented by Rh(3)/C$_3$N$_4$.

Comparative Example 4

Preparation of Rh(10)/PVP Heterogeneous Catalyst

A heterogeneous catalyst was prepared by immobilizing the rhodium complex prepared in 2) of Example 1 on a polymer support. Here, 0.040 g of the rhodium complex and 0.360 g of the polymer support poly(4-vinylpyridine) (PVP) were used in 3) of Example 1 so that the amount of the rhodium complex was 10 wt % based on the weight of the support. The catalyst prepared by the method of Comparative Example 4 was represented by Rh(10)/PVP.

Comparative Example 5

Preparation of Rh(10)/SBA-15 Heterogeneous Catalyst

A heterogeneous catalyst was prepared by immobilizing the rhodium complex prepared in 2) of Example 1 on a SBA-15 support. Here, 0.040 g of the rhodium complex and 0.360 g of the SBA-15 support were used in 3) of Example 1 so that the amount of the rhodium complex was 10 wt % based on the weight of the support. The catalyst prepared by the method of Comparative Example 5 was represented by Rh(10)/SBA-15.

Comparative Example 6

Preparation of Rh(10)/C Heterogeneous Catalyst

A heterogeneous catalyst was prepared by immobilizing the rhodium complex prepared in 2) of Example 1 on an activated carbon support. Here, 0.040 g of the rhodium complex and 0.360 g of the activated carbon support were used in 3) of Example 1 so that the amount of the rhodium complex was 10 wt % based on the weight of the support. The catalyst prepared by the method of Comparative Example 6 was represented by Rh(10)/C.

Test Example

Preparation of Acetic Acid through Methanol Carbonylation Reaction

The methanol carbonylation reaction was carried out using the heterogeneous catalyst of each of Examples 1 to 4 and Comparative Examples 1 to 6.

The carbonylation reaction was progressed in a 125 mL batch-type high-pressure reactor equipped with a Teflon vessel. 8 mL of a methanol reactant, 10 mL of an iodomethane promoter, 2 mL of deionized water, and 0.1 g of the heterogeneous catalyst were used. For high-pressure reaction, a gas mixture comprising a carbon monoxide reactant and an internal standard material nitrogen at a molar ratio of CO:N$_2$=90:10 was fed at a pressure of 40 bar to allow the reaction to occur. The reactants were heated with stirring at a rate of 100 rpm until the internal temperature of the reactor reached 135° C. When the internal temperature of the reactor reached 135° C., the heating process was terminated and the stirring rate was increased to 300 rpm, and a carbonylation reaction was progressed for 7 hr. After the reaction time of 7 hr, at which the methanol conversion was stable, the samples were taken and calculated for methanol conversion and selectivity. The results are shown in Table 1 below.

TABLE 1

| No. | Catalyst | Methanol conversion (carbon mol %) | Selectivity (mol %) | | | Acetic acid yield[3] (mol %) |
|---|---|---|---|---|---|---|
| | | | Acetic acid | MAc[1] | Others[2] | |
| Ex. 1 | Rh(5)/C$_3$N$_4$ | 98.5 | 77.0 | 22.9 | 0.1 | 75.8 |
| Ex. 2 | Rh(7)/C$_3$N$_4$ | 99.6 | 87.4 | 10.2 | 2.4 | 87.0 |
| Ex. 3 | Rh(10)/C$_3$N$_4$ | 98.2 | 81.7 | 11.3 | 7.0 | 80.2 |
| Ex. 4 | Rh(30)/C$_3$N$_4$ | 99.8 | 87.7 | 0.6 | 11.7 | 87.5 |
| C. Ex. 1 | Rh(0)/C$_3$N$_4$ | 19.8 | 29.0 | 2.3 | 67.6 | 5.7 |
| C. Ex. 2 | Rh(1)/C$_3$N$_4$ | 66.3 | 67.5 | 32.2 | 0.3 | 44.8 |
| C. Ex. 3 | Rh(3)/C$_3$N$_4$ | 86.8 | 72.0 | 18.7 | 9.3 | 62.5 |
| C. Ex. 4 | Rh(10)/PVP | 99.0 | 71.3 | 25.9 | 2.8 | 70.6 |
| C. Ex. 5 | Rh(10)/SBA-15 | 96.7 | 75.2 | 24.3 | 0.5 | 72.7 |
| C. Ex. 6 | Rh(10)/C | 95.3 | 73.9 | 25.7 | 0.4 | 70.5 |

[1]MAc: Methyl Acetate selectivity
[2]Others: mainly analyzed as acetone
[3]Yield = (Methanol conversion) * (Acetic acid selectivity)

As is apparent from Table 1, the catalysts of Examples 1 to 4 were the heterogeneous catalyst of the present invention, in which the amount of the rhodium complex immobilized on the carbon nitride support was 5 to 30 wt % based on the weight of the support and also in which commercially available rhodium chloride was immobilized in an amount of 10 wt % based on the weight of the support, thereby exhibiting superior catalytic activity such that the methanol conversion was 98.5 mol % or more and the acetic acid selectivity was 77.0 mol % or more.

In contrast, the catalyst of Comparative Example 1 having no rhodium active metal loaded thereon or the catalysts of Comparative Examples 2 and 3, in which the rhodium complex was immobilized in small amounts of 1 wt % and 3 wt %, respectively, were remarkably low in methanol conversion and acetic acid selectivity compared to the catalysts of Examples 1 to 4.

Also, in the catalysts of Comparative Examples 4 and 5, in which the rhodium complex was immobilized on the PVP polymer and the SBA-15 support, respectively, the acetic acid selectivity was slightly decreased compared to the catalysts of Examples 1 to 4.

Also, in the catalyst of Comparative Example 6, in which the rhodium complex was immobilized on the activated carbon support, the reactant methanol conversion and the product acetic acid selectivity were decreased and the byproduct methyl acetate selectivity was increased compared to the catalysts of Examples 1 to 4.

Meanwhile, FIG. 1 is a graph showing the results of comparison of acetic acid selectivity depending on the amount of the rhodium complex in the reaction using the Rh/g-$C_3N_4$ heterogeneous catalyst and acetic acid selectivity in the reaction using the Rh(10)/PVP heterogeneous catalyst. As shown in FIG. 1, the Rh/g-$C_3N_4$ heterogeneous catalyst in which the amount of the rhodium complex is 3 to 30 wt % based on the weight of the carbon nitride support can be found to exhibit superior catalytic activity compared to the Rh(10)/PVP heterogeneous catalyst.

The invention claimed is:

1. A method of preparing a Rh/$C_3N_4$ heterogeneous catalyst, comprising:
   (S1) preparing a carbon nitride support by heating a melamine resin serving as a carbon source to 500 to 550° C. in a nitrogen atmosphere,
   wherein the preparing the carbon nitride support in (S1) is performed by heating the melamine resin serving as the carbon source in a nitrogen atmosphere in a manner in which a reaction temperature is increased to 200 to 250° C. at a heating rate of 1 to 3° C./min, maintained for 20 to 40 min, further increased to 300 to 350° C. at a heating rate of 1 to 3° C./min, maintained for 20 to 40 min, additionally increased to 500 to 550° C. at a heating rate of 1 to 3° C./min, and maintained for 200 to 300 min;
   (S2) preparing a rhodium complex by reacting a rhodium compound with 3-benzoylpyridine; and
   (S3) preparing a Rh/$C_3N_4$ heterogeneous catalyst by immobilizing, on the carbon nitride support prepared in (S1), the rhodium complex prepared in (S2).

2. The method of claim 1, wherein the carbon nitride support prepared in (S1) has a specific surface area of 5 to 250 $m^2$/g.

3. The method of claim 1, wherein the rhodium compound used in (S2) is dichloro tetracarbonyl dirhodium ($O_4C_4Cl_2Rh_2$).

4. The method of claim 1, wherein in (S3), the rhodium complex is immobilized in an amount of 5 to 30 wt % based on a weight of the carbon nitride support.

* * * * *